United States Patent [19]

Moriya et al.

[11] Patent Number: 5,112,902
[45] Date of Patent: May 12, 1992

[54] PROCESS FOR PREPARING PARTICLES OF HIGH WATER-ABSORBENT RESIN

[75] Inventors: Tetsuo Moriya, Takatsuki; Susumu Kondo; Shinji Sanuki, both of Kyoto, all of Japan

[73] Assignee: Nippon Gohsei Kagaku Kogyo Kabushiki Kaisha, Osaka, Japan

[21] Appl. No.: 524,771

[22] Filed: May 17, 1990

[30] Foreign Application Priority Data

May 24, 1989 [JP] Japan .................... 1-131203

[51] Int. Cl.$^5$ ............ C08J 3/00; C08L 29/04; C08G 63/48; C08F 283/00
[52] U.S. Cl. .................... 524/503; 524/916; 525/57; 525/201; 525/221; 525/522; 528/490; 528/494; 528/495; 528/501; 528/502
[58] Field of Search .......... 524/916, 503; 528/490, 528/494, 495, 501, 502; 525/201, 57, 221, 522

[56] References Cited

U.S. PATENT DOCUMENTS

| | | | |
|---|---|---|---|
| 4,408,040 | 10/1983 | Flock et al. | 528/502 |
| 4,483,950 | 11/1984 | Fanta et al. | 524/47 |
| 4,525,581 | 6/1985 | Denzinger et al. | 528/502 |
| 4,542,176 | 9/1985 | Graham | 528/502 |
| 4,668,715 | 5/1987 | Phillips | 524/916 |
| 4,732,968 | 3/1988 | Obayashi et al. | 528/490 |
| 4,845,192 | 7/1989 | Sortwell et al. | 528/502 |

FOREIGN PATENT DOCUMENTS 2082614A 3/1982 United Kingdom.
2162525 2/1986 United Kingdom.

*Primary Examiner*—Paul R. Michl
*Assistant Examiner*—Patrick Niland
*Attorney, Agent, or Firm*—Armstrong & Kubovcik

[57] ABSTRACT

A process for preparing particles of a high water-absorbent resin which comprises mixing a powder of a high water-absorbent resin having a water content of 10 to 60% by weight with a powder of water-soluble high molecular weight compound and drying the mixture. The obtained particles according to the present invention are suitable for use of sanitary goods, water-retaining agents or soil conditioner in the fields of agriculture and horticulture and other various uses.

6 Claims, No Drawings

PROCESS FOR PREPARING PARTICLES OF HIGH WATER-ABSORBENT RESIN

BACKGROUND OF THE INVENTION

The present invention relates to a process for preparing particles of a high water-absorbent resin, and more particularly to a process for preparing particles of a high water-absorbent resin which is suitably used as agents for improving water absorption used in sanitary goods such paper diapers, sanitary napkins, tampons and disposable dustclothes, water-retaining agents or soil conditioners in the fields of agriculture and horticulture, and other various uses of coagulation of sludge, prevention of dew condensation on building materials, dehydration of oil, and so on.

Water-absorbent resins have, hitherto, been used in the manufacture of paper diapers, sanitary napkins, tampons, disposable dustcloths and other sanitary goods, and as water-retaining agents or soil conditioners in the fields of agriculture and horticulture. They have been also used for the purpose of coagulation of sludge, prevention of dew condensation on building materials, dehydration of oil, and so on.

These known water-absorbent resins include crosslinked polyacrylic acid salts, hydrolyzates of crosslinked acrylic acid ester-vinyl acetate copolymers, crosslinked starch-acrylic acid salt graft copolymer, hydrolyzates of crosslinked starch-acrylonitrile graft copolymers, crosslinked polyvinyl alcohol grafted with maleic anhydride, crosslinked polyethylene oxide, and so on.

These high water-absorbent resin powders are prepared in a manner wherein a high water-absorbent polymer is prepared in reversed phase suspension polymerization, reversed phase emulsion polymerization, aqueous solution polymerization or a polymerization using an organic solvent, then the prepared polymer is dried as it is, further, when occasion demands, the dried one is pulverized.

The high water-absorbent resin powders prepared by the above-mentioned manners, however, have a good many fine particles which can pass through a 100 mesh standard sieve. Thus, such high water-absorbent resin powders have the following defects (1) It is easy to generate dust, the working surrounding becomes easily bad and final products easily loss in weight.

(2) The miscibility and dispersibility of the resin powder with an other material are bad.

(3) It is easy to make undissolved lumps of the resin powder when contacting with liquid (4) Bridging and flushing are easily caused in a hopper due to poor fluidity of the resin powder For solving the above-mentioned defects, it have been proposed to remove fine particles or to prepare resin particles by using a binder. The former method is economically disadvantage and the later method is in danger of catching fire in drying step of the obtained particles when using an organic binder. Also, if insufficiently drying, the final particles are problematic in safety to human bodies due to the remaining organic solvent therein. When using as the binder an aqueous liquid such as water alone, an aqueous mixture of water and an organic solvent compatible with water or an aqueous solution wherein a water-soluble high molecular weight compound is dissolved in water or the aqueous mixture as mentioned above, though there is no problem caused in the case that the organic solvent is used as the binder, it is difficult to uniformly mix or disperse the particles with or in the aqueous liquid and big lumps of the resin particles, having high density (hereinafter referred to as "block") are produced in the obtained particles because of high rate of water absorption of the particles, thus resulting in that it is difficult to finally obtain uniform particles.

As a process for preparing particles of a water-absorbent resin which improves the above-mentioned defects, there are processes described in Japanese Unexamined Patent Publication No. 61-97333 and No. 61-101536, wherein a mixture of a high water-absorbent resin powder and an inorganic powder is stirred by using a specific apparatus, and to the mixture is added the aqueous liquid containing binder. According to these processes it is required to supply the aqueous liquid in the state of a fine droplet for uniformly mixing the high water-absorbent resin particles with the aqueous liquid. When using the water-soluble high molecular weight compound as the binder, however, for supplying the aqueous liquid in the state of a fine droplet, it is necessary to make the amount of the binder small or to dissolve the binder in a large amount of water because of its high viscosity. Thus, the obtained particles are poor in strength or it is required to expend much time and much energy for drying them. Further, if the aqueous liquid is not supplied in the state of a fine droplet to the resin particles stirred at high speed by using the specific apparatus, the blocks are caused partially.

It is an object of the present invention is to provide a process for preparing particles of a high water-absorbent resin which do not have fine particles unsuitable for practical use and have high rate of water absorption.

This and other objects of the present invention will become apparent from the description hereinafter.

SUMMARY OF THE INVENTION

In accordance with the present invention, there is provided a process for preparing particles of a high water-absorbent resin which comprises: mixing a powder of a high water-absorbent resin having a water content of 10 to 60 % by weight with a powder of a water-soluble high molecular weight compound, and drying the mixture.

According to the process of the present invention, the conventional defects that the obtained high water-absorbent resin particles contain many fine particles unsuitable for practical use, there is a danger that the resin particles catch fire in drying step, the safety to human bodies is problematic due to the remaining organic solvent in the resin particles, and in the final resin particles, the blocks are partially caused are solved, moreover, the obtained resin particles contain many particles having a particle size suitable for practical use and are high in rate of water absorption.

DETAILED DESCRIPTION

The high water-absorbent resins used in the present invention are not particularly limited and known water-absorbent resins can be used without any limitation. Examples of the high water-absorbent resins are, for instance, crosslinked polyacrylic acid salts, hydrolyzates of crosslinked acrylic acid ester-vinyl acetate copolymers, crosslinked starch-acrylic acid salt graft copolymer, hydrolyzates of crosslinked starch-acrylonitrile graft copolymer, crosslinked polyvinyl alcohol grafted with maleic anhydride, crosslinked polyethylene oxide, and the like. Preferred among the high water-absorbent resins are the crosslinked polyacrylic acid salts, because the polymers are excellent in physical properties such as rate of water absorption.

These high water-absorbent resin powders are prepared, in general, by conducting a reversed phase suspension polymerization, reversed phase emulsion polymerization, aqueous solution polymerization or polymerization using an organic solvent to synthesize the high water-absorbent resin, and dring them, further pulvelizing the dried one when occasion demands.

The preparation method of the high water-absorbent resin powder used in the present invention is not limited to the above-mentioned methods and the resin powder may be prepared in any manner.

Also, in the present invention, as the high water-absorbent resin powder, there can be used the resin powder whose not only surface but also surface and inside is crosslinked by using a crosslinking agent disclosed in Japanese Unexamined Patent Publication No. 58-180233, No. 58-117222, and No. 58-42602 to increase the rate of water absorption and the dispersibility to water. Examples of the crosslinking agents are, for instance, an epoxy compound having the formula:

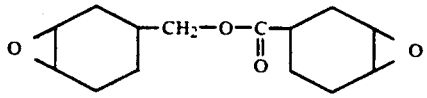

a condensation product of a long-chain dibasic acid and epichlorohydrin, a reaction product of bisphenol A and epichlorohydrin, and the like. It is preferable that the amount of the crosslinking agent is from 0.0005 to 3 parts by weight, more preferably from 0.01 to 1 part by weight, based on 100 parts by weight of the high water-absorbent resin powder which is the raw material. If the amount of the crosslinking agent is more than 3 parts by weight, it tends to lower the water absorbency thereof.

The average particle size of the high water-absorbent resin powder varies depending on the kinds and cannot be decided unqualifiedly. It is preferable that the average particle size of the high water-absorbent resin powder which is the raw material is from 100 to 500 $\mu$m, more preferably from 150 to 400 $\mu$m, in case of paying regard to the use as diapers. When the average particle size is more than 500 $\mu$m, the rate of water absorption is lowered. When the average particle size is less than 100 $\mu$m, dust is produced or undissolved lumps of the particles are produced if contacting the particles with liquid.

In the present invention, the water content of the high water-absorbent resin powder which is the raw material is adjusted to 10 to 60 % by weight, preferably from 15 to 50 % by weight, more preferably from 20 to 45 by weight. When the water content is within the above-mentioned range, the high water-absorbent resin powder is easily mixed with the water-soluble high molecular weight compound powder, the mixture is only dried with heating, without adding water to the mixture, to give the desired resin particles, the obtained particles have no block and have a suitable particle size for practical use (12 to 100 mesh).

The water-soluble high molecular weight compound generally contains water (the water content of the water-soluble high molecular weight compound about 10 % by weight). In the present invention, regardless of the above-mentioned water content, any water-soluble high molecular weight compound can be used so long as its normal state is a powder (the particle size: not more than 48 mesh).

The high water-absorbent resin powder is mixed with the water-soluble high molecular weight compound powder. Examples of the water-soluble high molecular weight compound are, for instance, polyvinyl alcohol (PVC) and its derivatives, polyacrylic acid and its salts, starch and its derivatives, cellulose and its derivatives, and the like. Among them, PVA is preferably used from the viewpoint of excellent binding property.

In the present invention, before mixing the high water-absorbent resin powder with the water-soluble high molecular weight, a sorbitan surfactant having an HLB (hydrophile-lyophile balance) of 2.0 to 4.7 dissolved in an organic solvent may be mixed with the high water-absorbent resin powder When the mixing as mentioned above is conducted, even if adding water to the mixture of the high water-absorbent resin powder and the water-soluble high molecular weight compound powder, the final resin particles have no block.

Examples of the sorbican surfactants having an HLB of 2.0 to 4.7 are, for instance, sorbican monostearate, sorbitan distearate, sorbitan monooleate, sorbitan dioleate, and the like. Among them, sorbitan monostearate and sorbitan distearate are preferable from the viewpoint of no coloring and no oder.

When the HLB of the sorbitan surfactant is less than 2.0, it tends to lower the rate of water absorption of the final water-absorbent resin particles. On the other hand, when the HLB is more than 4.7, it is impossible to uniformly mix the high water-absorbent resin powder with water when adding water to the resin powder with the surfactant, due to the small hydrophobic property of the surfactant.

The amount of the surfactant is from 50 to 5000 ppm, preferably from 100 to 1500 ppm, more preferably from 150 to 1000 ppm, based on the high water-absorbent resin powder which is the raw material. When the amount of the surfactant is less than 50 ppm, there is a tendency that it is difficult to uniformly admix the high water-absorbent resin powder with water. On the other hand, when the amount of the surfactant is more than 5000 ppm, there is a tendency that the rate of water absorption is too slow.

The surfactant is dissolved in the organic solvent. Examples of the organic solvents are, for instance, cyclohexane, hexane, benzene, toluene, xylene, and the like. Among them, n-hexane and cyclohexane are preferred from the viewpoint of easy drying after mixing. The amount of the organic solvent varies depending on the kinds of the high water-absorbent resin powder and the surfactant. Generally, the amount of the organic solvent is from 5 to 40 parts by weight, preferably from 15 to 25 parts by weight, based on 100 parts by weight of the high water-absorbent resin powder which is the raw material.

When using the organic solvent, before mixing the resin powder with the water-soluble high molecular weight compound powder, it is preferable that the organic solvent is previously volatilized from the high water-absorbent resin powder in a usual manner to lower the organic solvent content as low as possible. The content of the organic solvent remaining in the water-absorbent resin powder is adjusted to not more than 5 % by weight, preferably not more than 1 % by weight, more preferably not more than 0.5 % by weight. When the organic solvent content is more than 5 % by weight, the miscibility with the water-soluble high molecular weight compound powder becomes poor, and the sanitation and the safety of the final resin particles become problematic.

The water-soluble high molecular weight compound powder is mixed with the high water-absorbent resin power in an amount of 0.01 to 5 % by weight, preferably from 0.1 to 3 % by weight, more preferably from 0.1 to 1 % by weight of the high water-absorbent resin powder. When the amount of the water-soluble high molecular weight compound powder is less than 0.01 % by weight, it tends to lower the strength of the final resin particles. On the other hand, when the amount is more than 5 % by weight, it tends to lower the rate of water absorption and the water absorbency.

After mixing the high water-absorbent resin powder with the water-soluble high molecular weight compound powder, water may be added to the mixture if necessary in order to completely dissolve the water-soluble high molecular weight compound powder and increase the strength of the final resin particles. The kind of water to be used is not particularly limited. It is preferable to use a deionized water. The amount of water varies depending on the kinds of the used high water-absorbent resin powder and water-soluble high molecular weight compound and cannot be decided unqualifiedly. In any case, the amount of water is not more than 60 % by weight of the high water-absorbent resin powder.

After mixing the high water-absorbent resin powder with the water-soluble high molecular weight compound powder, the mixture is kneaded at room temperature to 80° C. for 0.5 to 1 hour, and dried with heating at a temperature capable of dissolving the water-soluble high molecular weight compound or higher in the atmosphere or in vacuo to give the final particles of the high water-absorbent resin. It is preferable that the mixture is dried at a temperature of 50° to 80° C for 1 to 2 hours in the atmosphere then is dried at a temperature of 50° to 90° C. for 1 to 2 hours in vacuo.

The particle size and shape of the final particles are not particularly limited Generally, a particle size of about 12 to 100 mesh is preferred.

The thus obtained particles of the high water-absorbent resin have no block and have scarcely the solvent, so are sanitary and safe. Further, the final particles have few fine particles, and have useful particle size such as about 12 to 100 mesh. Moreover, the particles are remarkably improved in rate of water absorption in comparison with the conventional particles.

The present invention is more specifically described and explained by means of the following Examples wherein all per cents and parts are by weight unless otherwise noted. It is to be understood that the present invention is not limited to the Examples, and various changes and modifications may be made in the invention without departing from the spirit and scope thereof.

REFERENCE EXAMPLE 1

Preparation of fine particles of sodium polyacrylate by reversed phase suspension polymerization A 500 ml beaker was charged with 100 g of acrylic acid, and it was neutralized with 157 g of a 25.9 aqueous solution of sodium hydroxide at not more than 35° C. under cooling to give an aqueous solution of partially neutralized acrylic acid wherein 73 % by mole of acrylic acid was neutralized. A 300 ml dropping funnel was charged with the obtained aqueous solution of partially neutralized acrylic acid and it was bubbled for 30 minutes by using nitrogen gas. Then, to the aqueous solution were added 3 m: of a 7 % aqueous solution of APS (ammonium persulfate) and 1 m: of a 1 % aqueous solution of N,N'-methylenebis(acrylamide), and the mixture was thoroughly mixed to give a mixed aqueous solution of the aqueous solution of the partially neutralized acrylic acid, APS and N,N'-methylenebis(acrylamide).

Separately, a 2 : separable flask was charged with 760 m± of cyclohexane, in which 4 g of sorbitan monostearate having an HLB of 4.7 was dissolved. Then the cyclohexane solution of sorbitan monostearate was bubbled at 25° C.. for 30 minutes by using nitrogen gas (total volume of nitrogen gas: 10 :) to remove dissolved oxygen in the solution and air in the space of the flask from the flask. The internal temperature of the flask was raised to 72° C., and the mixed aqueous solution of the aqueous solution of the partially neutralized acrylic acid, APS and N,N'-methylenebis(acrylamide) obtained as above was added dropwise over 1 hour to the separable flask with stirring to polymerize. Further the polymerization was continued at 72° C. over 3 hour to complete the polymerization. Then, the polymerization mixture was cooled down to room temperature and the produced particles were filtered off from the polymerization mixture by using a 325-mesh wire net. Then, the particles were dried at 90° C. for 0.5 hour in vacuo to give a high water-absorbent resin powder, which was a crosslinked sodium polyacrylate having a water content of 35 %. The high water-absorbent resin powder was in the form of pearly particles and had an average particle size of 110 μm.

REFERENCE EXAMPLE 2

Preparation of sodium polyacrylate by aqueous solution polymerization in static state The same mixed aqueous solution of the aqueous solution of partially neutralized acrylic acid, ASP and N,N'-methylenebis(acrylamide) as obtained in Reference Example 1 was obtained in the same manner as in Reference Example 1.

Separately, an open side (upper side) of a flat bottom stainless steel vat (200 mm ×150 mm) was completely sealed with a polyester sheet, and a hole having a diameter of about 10 mmφ was made on the center of the sheet. A rubber hosepipe was attached to the vat through the hole, and nitrogen gas was supplied to the vat via the hosepipe to thoroughly substitute nitrogen gas for air in the space of the vat.

The mixed aqueous solution obtained as above was poured into the vat, then the vat was dipped in a warm bath having a temperature of 60° C., and the polymerization was conducted. After about 10 minutes, the internal temperature of the vat reached to the maximum temperature, 105° C. The vat was dipped in a warm bath having a temperature of 60° C. over 2 hours, then was cooled down to a temperature of 30° C. to give a sheet of a crosslinked sodium polyacrylate. The obtained sheet was taken out from the vat, and was cut off with scissors to give chips. The chips were dried in a vacuum drier having a temperature of 90° C. for 30 minutes. The dried chips were pulverized by using a pulverizer and a powder having a particle size of 70 to 200 mesh was separated from the pulverized chips.

REFERENCE EXAMPLE 3

The procedure of Reference Example 1 was repeated except that N,N'-methylenebisacrylamide was not used to give pearly, fine sodium polyacrylate particles having an average particle size of 110 μm and a water content of 25 %. Then, the obtained sodium polyacrylate particles were filtered off from the polymerization mixture under reduced pressure by using a Neutsche funnel, a filtering flask and a filter paper. The flask was charged with the obtained high water-absorbent resin powder and 1 l of cyclohexane, and the mixture was stirred at 30° C. for 30 minutes and was filtered under reduced pressure by using a Neutsche funnel, a filtering flask and a filter paper. The procedure of the addition of cyclohexane to the resin powder, then the stirring of the mixture and finally the filtration was repeated 5 times to completely remove sorbitan monostearate from the obtained resin powder.

EXAMPLE 1

A 1 l kneader was charged with 200 g of the cross-linked sodium polyacrylate in the state of fine particles having an average particle size of 110 μm, obtained in Reference Example 1, to which 1.0 g of PVA particles (commercially available from Nippon Gohsei Kagaku Kogyo Kabushiki Kaisha, passing through 150 mesh seive, degree of hydrolysis: not less than 99.6 % by mole, average degree of polymerization 1800) was added with kneading and the mixture was kneaded for 30 minutes. Then, the temperature was raised to 70° C. and the mixture was maintained at 70° C. for 1 hour. After opening the lid of the kneader, the mixture was dried for 1 hour in the atmosphere, then dried at 90° C. for 1.5 hours in a vacuum drier to give particles of the high water-absorbent resin.

As to the high water-absorbent resin powder, the water content was measured as follows Water content (%)

An aluminum foil cup (80 mmφ×30 mmH) was charged with 10 g of a high water-absorbent resin powder to be measured the water content, and it was dried at 90° C. for 4 hours in a vacuum drier. The water content was calculated according to the following equation.

$$\text{Water content (\%)} = \frac{10 - \text{(Weight of the dried resin powder)}}{\text{Weight of the dried resin powder}} \times 100$$

The obtained particles were separated by using a 12-mesh wire net and a 100-mesh wire net. As a result, it was confirmed that useful particles having a particle size of 12 mesh to 100 mesh account for 94 % of the total of the obtained particles, that is, the process for preparing particles of the present invention was excellent in granulation property.

As to the resin particles having a particle size of 12 to 100 mesh, the ratio of synthetic urine absorption, the absorption ratio, and the urine diffusion were measured as follows The results are shown in Table 1 with the particle size distribution of the final particles.

Rate of synthetic urine absorption (g/g 3 minutes)

As to the final particles having a particle size of 12 to 100 mesh, the rate of synthetic urine absorption was measured according to a tea bag method.

Absorption ratio concerning physiological saline water or deionized water (times)

To a 500 ml beaker were added 0.2 g of the dried final resin particles and 60 g of physiological saline water (0.9 % aqueous solution of sodium chloride) or 200 g of deionized water. After the mixture was lightly stirred with a glass bar, it was allowed to stand for 1 hour at room temperature, and the particles were filtered off through a 325-mesh wire net. The weight of the gel remaining on the net was measured and the absorption ratio was calculated according to the following equation.

$$\text{Absorption ratio} = \frac{[\text{Weight of the gel remaining on the net (g)}] - [\text{Weight of the dried final particles (0.2 g)}]}{[\text{Weight of the dried final particles (0.2 g)}]}$$

Urine diffusion (mm)

Five grams of the final resin particles were uniformly scattered on the center of a sheet of a fleecy pulp (length: 120 mm, width: 280 mm, thickness: 5 mm) in an area of 100 mm ×240 mm, on which the same sheet as above was placed, and the surface was lightly pressed to give a diaper for testing A dropping funnel was attached to the center of the diaper for testing and 200 m: of the synthetic urine was poured into the diaper. After 30 minutes the upper fleecy pulp sheet was removed, the length [diffusion length (mm)]of the area wherein the swollen resin particles with the synthetic urine were placed was measured. The urine diffusion is an important physical property, as to goods having an absorption band such as diapers, because the longer the diffusion length, the more excellent the absorption of the high water-absorbent resin particles.

EXAMPLE 2

Particles of a high water-absorbent resin were prepared in the same manner as in Example 1 except that 2 g of sodium polyacrylate (commercially available under the trade mark "A-20P3", from Toa Gohsei Kagaku Kogyo Kabushiki Kaisha, passing through 110 mesh seive, average degree of polymerization: 40000) was used instead of the PVA particles.

As to the particles, the physical properties were measured in the same manner as in Example 1.

The results are shown in Table 1 with the particle size distribution.

EXAMPLE 3

A 1 l kneader was charged with 200 g of the sodium polyacrylate in the state of fine particles having a water content of 25 % and an average particle size of u 110 μm, obtained in Reference Example 3, and a solution composed of 0.1 g of sorbitan monostearate having an HLB of 4.7, 0.04 g of an epoxy compound having the formula:

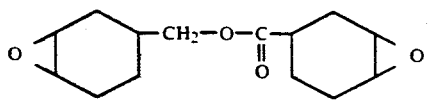

and 50 g of cyclohexane was added to the kneader. After mixing, cyclohexane was removed from the mixture at 40° C. under reduced pressure to give the sodium polyacrylate powder having the cyclohexane content of not more than 0.5 %.

Then, the same PVA particles as used in Example 1 was added to the kneader in an amount of 2.0 g and 30 g of deionized water was added thereto, and the mixture was kneaded at 75° C. for 1 hour. It was dried for 1 hour in the atmosphere, opening the lid of the kneader, then dried at 90° C. for 1.5 hours in a vacuum drier to give particles of the high water-absorbent resin The content of remaining cyclohexane in sodium polyacrylate powder was calculated as follows Content of remaining solvent (%)

A 30 ml glass bottle was charged with 1 g of a high water-absorbent resin powder to be measured the content of the solvent remaining therein, to which 10 ml of methanol was added, and the flask was allowed to stand for 3 hour while it was lightly shaked at intervals. The content of the solvent remaining in the high water-absorbent resin powder was measured by gas chromatography of the supernatant liquid in the flask.

EXAMPLE 4

The procedure of Example 3 was repeated except that a high water-absorbent resin powder having a water content shown in Table 1 was used and PVA was used in an amount shown in Table 1 to give particles of high water-absorbent resin.

As to the obtained particles, the physical properties were measured in the same manner as in Example 1.

The results are shown in Table 1 with the particle size distribution.

EXAMPLES 5 and 6

The procedure of Example 1 was repeated except that a high water-absorbent resin powder having a water content shown in Table 1 was used and PVA particles were used in an amount shown in Table 1 to give particles of high water-absorbent resin.

As to the obtained particles, the physical properties were measured in the same manner as in Example 1.

The results are shown in Table 1 with the particle size distribution.

COMPARATIVE EXAMPLES 1 and 2

The procedure of Example 1 was repeated except that as the high water-absorbent resin powder, one having a water content of 5 %, which was obtained by drying the crosslinked sodium polyacrylate powder obtained in Reference Example 1 (Comparative Example 1), or one having a water content of 5 %, which was obtained by drying the crosslinked sodium polyacrylate powder obtained in Reference Example 2 (Comparative Example 2) to give particles of high water-absorbent resin.

As to the obtained particles, the physical properties were measured in the same manner as in Example 1.

The results are shown in Table 1 with the particle size distribution.

TABLE 1

| Ex. No. | Water content of the high water-absorbent resin powder (%) | Water-soluble high molecular weight compound Kind | Amount (%)*1 | Amount of the surfactant (%)*2 |
| --- | --- | --- | --- | --- |
| Ex. 1 | 35 | PVA | 0.5 | — |
| Ex. 2 | 35 | Sodium polyacrylate | 1.0 | — |
| Ex. 3 | 25 | PVA | 1.0 | 0.05 |
| Ex. 4 | 25 | PVA | 0.5 | 0.05 |
| Ex. 5 | 55 | PVA | 0.5 | — |
| Ex. 6 | 35 | PVA | 0.05 | — |
| Com. Ex. 1 | 5 | PVA | 0.5 | — |
| Com. Ex. 2 | 5 | PVA | 0.5 | — |

| Ex. No. | Particle size distribution of the final particles | | | Physical properties of the final particles |
| --- | --- | --- | --- | --- |
| | More than 12 mesh (%) | From 12 to 100 mesh (%) | Less than 100 mesh (%) | Rate of synthetic urine absorption (g/g · 3 minutes) |
| Ex. 1 | 4 | 94 | 2 | 35 |
| Ex. 2 | 5 | 93 | 2 | 30 |
| Ex. 3 | 5 | 94 | 1 | 35 |
| Ex. 4 | 0 | 65 | 35 | 35 |
| Ex. 5 | 30 | 68 | 2 | 34 |
| Ex. 6 | 3 | 85 | 12 | 34 |
| Com. Ex. 1 | 0 | 5 | 95 | 5 |
| Com. Ex. 2 | 0 | 25 | 75 | 5 |

| Ex. No. | Physical properties of the final particles | | |
| --- | --- | --- | --- |
| | Absorption ratio (times) | | Urine diffusion (mm) |
| | Deionized water | Physiological saline water | |
| Ex. 1 | 600 | 53 | 170 |
| Ex. 2 | 650 | 55 | 160 |
| Ex. 3 | 650 | 55 | 200 |
| Ex. 4 | 600 | 53 | 160 |
| Ex. 5 | 600 | 53 | 170 |
| Ex. 6 | 600 | 53 | 170 |
| Com. Ex. 1 | 600 | 53 | 120 |
| Com. Ex. 2 | 630 | 53 | 110 |

(Notes)
*1 % based on the powder of the high water-absorbent resin (raw material)
*2 % based on the powder of the high water-absorbent resin (raw material)

The results of Table 1 show that as to the particles of the high water-absorbent resin obtained in Examples 1-6, particles having a useful particle size of 12 to 100 mesh account for not less than 65 % of the total of the obtained final particles, and they are more excellent in granulation property than those obtained in Comparative Examples 1 and 2. Moreover, the final particles obtained in Examples 1 to 6 are remarkably superior in rate of synthetic urine absorption, absorption ratio concerning deionized water, absorption ratio concerning physiological saline water and urine diffusion to the final particles obtained in Comparative Examples 1 and 2.

According to the process of the invention, the obtained particles have no block; since the solvent remains scarcely in the particles, the particles are sanitary and safe; since the obtained particles have few fine particles and have a useful particle size distribution, goods produced by using the particles do not lose in weight and the working surrounding is not made bad; and since the particles are excellent in miscibility, dispersibility and fluidity, bridging or flushing is scarcely caused in a hopper and dissolved lumps of the particles are not produced. Further, the particles are suitable for various use in sanitary goods and water-retaining agents or soil conditioners in the fields of agriculture and horticulture because of higher rate of water absorption compared to conventional goods in addition to the excellent properties as mentioned above.

In addition to the ingredients used in the Examples, other ingredients can be used in the Examples as set forth in the specification to obtain substantially the same results.

What we claim is:

1. A process for preparing particles of a high water-absorbent resin which comprises:
   adjusting the water content of a powder of a highly water-absorbent resin to from 10 to 60% by weight, based on the weight of the resin;
   mixing said powder of highly water-absorbent resin with 0.01 to 5% by weight, based on the weight of said resin, of a powder of a water-soluble high molecular weight compound to form a mixture consisting essentially of said powders; and
   drying said mixture of powders.

2. The process of claim 1, wherein the highly water-absorbent resin powder is a crosslinked polyacrylic acid salt powder.

3. A process for preparing particles of a highly water-absorbent resin which comprises:
   adjusting the water content of a powder of a highly water-absorbent resin to from 10 to 60% by weight, based on the weight of the resin;
   mixing the powder of the highly water-absorbent resin having a water content of from 10 to 60% by weight with a solution of a sorbitan surfactant having a HLB of 2.0 to 4.7 in an organic solvent and then volatilizing the solvent to from a mixture of the surfactant with the resin containing not more than 5% by weight of the organic solvent;
   mixing said mixture of the surfactant with the highly water-absorbent resin having a water content of from 10 to 60% by weight and containing not more than 5% by weight of the organic solvent with 0.01 to 5% be weight, based on the weight of said resin, of a powder of a high molecular weight water-soluble compound to from a mixture consisting essentially of said powders; and
   drying said mixture of powders.

4. The process of claim 3, wherein the highly water-absorbent resin powder is a crosslinked polyacrylic acid salt powder.

5. A process for preparing particles of a highly water-absorbent resin which comprises:
   adjusting the water content of a powder of a highly water-absorbent resin to form 10 to 60% by weight, based on the weight of the resin;
   mixing the powder of the highly water-absorbent resin having a water content of from 10 to 60% by weight with a solution of a sorbitan surfactant having a HLB of 2.0 to 4.7 in an organic solvent and then volatilizing the solvent to form a mixture of the surfactant with the resin containing not more than 5% by weight of the organic solvent;
   mixing said mixture of the surfactant with the highly water-absorbent resin having a water content of from 10 to 60% by weight and containing not more than 5% by weight of the organic solvent with 0.01 to 5% be weight, based on the weight of said resin, of a powder of a high molecular weight water-soluble compound to form a mixture consisting essentially of said powders; adding water to said mixture of powders; and
   drying said mixture of powders.

6. The process of claim 3, wherein the highly water-absorbent resin powder is a crosslinked polyacrylic acid salt powder.

* * * * *